United States Patent [19]

Tomioka et al.

[11] Patent Number: 4,668,693

[45] Date of Patent: May 26, 1987

[54] BROMODICHLOROIMIDAZOLE INSECTICIDE

[75] Inventors: Hiroki Tomioka, Takarazuka; Toshihiko Yano, Ikoma; Hisami Takeda, Kakogawa; Naonori Hirata, Sakai, all of Japan

[73] Assignee: Sumitomo Chemical Company, Limited, Osaka, Japan

[21] Appl. No.: 797,942

[22] Filed: Nov. 14, 1985

[30] Foreign Application Priority Data

Nov. 22, 1984 [JP] Japan .................. 59-247381
May 31, 1985 [JP] Japan .................. 60-119498
Jun. 7, 1985 [JP] Japan .................. 60-124708

[51] Int. Cl.$^4$ .................. A01N 43/50; C07D 233/66
[52] U.S. Cl. .................. 514/399; 548/337
[58] Field of Search .................. 548/337; 514/399

[56] References Cited

U.S. PATENT DOCUMENTS 3,409,606 11/1968 Williams et al. .................. 548/337
3,674,874 7/1972 Rutz et al. .................. 548/337

FOREIGN PATENT DOCUMENTS 1316665 5/1973 United Kingdom .................. 548/337

OTHER PUBLICATIONS

J. Heterocyclic Chemistry, vol. 4, 399–402 (1967).

*Primary Examiner*—John M. Ford
*Assistant Examiner*—Robert C. Whittenbaugh
*Attorney, Agent, or Firm*—Stevens, Davis, Miller & Mosher

[57] ABSTRACT

A bromodichloroimidazole derivative represented by the formula

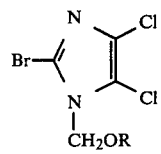

wherein R represents a $C_1$–$C_4$ alkyl, $C_2$–$C_5$ alkyl substituted by one or more halogen atoms, $C_3$ alkenyl, $C_3$ alkenyl substituted by one or more halogen atoms, $C_3$ alkynyl or $C_3$ alkynyl group substituted by one or more halogen atoms; its production; and an insecticidal and/or acaricidal composition containing it as an active ingredient.

20 Claims, No Drawings

BROMODICHLOROIMIDAZOLE INSECTICIDE

The present invention relates to a bromodichloroimidazole derivative represented by the formula (I) (hereinafter referred to as present compound),

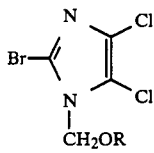

wherein R represents a $C_1$–$C_4$ alkyl, $C_2$–$C_5$ alkyl substituted by one or more halogen atoms (e.g. chlorine, bromine, iodine and fluorine), $C_3$ alkenyl, $C_3$ alkenyl substituted by one or more halogen atoms (e.g. chlorine, bromine, iodine and fluorine), $C_3$ alkynyl or $C_3$ alkynyl group substituted by one or more halogen atoms (e.g. chlorine, bromine, iodine and fluorine), its production and an insecticidal and/or acaricidal composition containing it as an active ingredient.

It is described in B.P. No. 1,316,665, U.S. Pat. No. 3,674,874, etc. that a certain kind of trihaloimidazole derivative, for example 1-n-pentyloxymethyl-2,4,5-trichloroimidazole, 1-isopropoxymethyl-2,4,5-trichloroimidazole, etc., can be used as an active ingredient for insecticidal and/or acaricidal compositions. It may not always be said, however, that these compounds are always satisfactory as such active ingredient.

The present inventors extensively studied to find a compound having a more superior insecticidal and/or acaricidal activity, and as a result, found that the present compound represented by the formula (I) has excellent properties as follows:

1. Insecticidal and/or acaricidal activity is very high.
2. Activity against cockroaches is particularly high.
3. Activity against insecticide resistant colony is also high.
4. Effect as fumigants is high.

The present inventors thus completed the present invention.

The present compound has particularly a high activity against cockroaches such as German cockroach (*Blattella germanica*), American cockroach (*Periplaneta americana*), smoky brown cockroach (*Periplaneta fuliginosa*), etc.

The present compound, therefore, can be used as an active ingredient for insecticidal and/or acaricidal compositions which display an effect on insect pests in question in many scenes. Particularly, it is expected to be used as an active ingredient for cockroach-controlling fumigants.

In the present compound represented by the formula (I), preferred compounds are those in which R is a $C_1$–$C_4$ alkyl, $C_2$–$C_4$ alkyl substituted by one or more halogen atoms, $C_3$ alkenyl or $C_3$ alkynyl group, and more preferred ones include:

1-methoxymethyl-2-bromo-4,5-dichloroimidazole,
1-n-propyloxymethyl-2-bromo-4,5-dichloroimidazole,
1-isopropyloxymethyl-2-bromo-4,5-dichloroimidazole,
1-(4-bromobutyloxymethyl)-2-bromo-4,5-dichloroimidazole,
1-(4-chlorobutyloxymethyl)-2-bromo-4,5-dichloroimidazole, etc.

As a compound for cockroach-controlling fumigants, 1-(4-bromobutyloxymethyl)-2-bromo-4,5-dichloroimidazole is particularly preferred.

The present compounds can be produced by reacting 2-bromo-4,5-dichloroimidazole with a halomethyl ether represented by the formula (II), $$XCH_2\text{—}OR \qquad (II)$$

wherein X represents a halogen atom (e.g. chlorine and bromine), and R has the same meaning as described above, at about 0° C. to about 150° C. for about 1 to about 24 hours in a solvent in the presence of a dehydrohalogenating agent.

The present compounds can also be produced by reacting a halomethylbromodichloroimidazole represented by the formula (III),

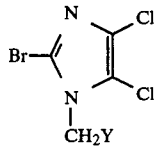

wherein Y represents a halogen atom (e.g. chlorine, bromine), with an alcohol represented by the formula (IV), $$HOR \qquad (IV)$$

wherein R has the same meaning as described above, at about 0° C. to about 150° C. for about 1 to about 24 hours in a solvent in the presence of a dehydrohalogenating agent.

The solvent used in this reaction includes for example aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), alcohols (e.g. methanol, ethanol, propanol, butanol, allyl alcohol, propargyl alcohol), esters (e.g. ethyl formate, ethyl acetate, butyl acetate, diethyl carbonate), nitro compounds (e.g. nitroethane, nitrobenzene), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, N,N-dimethylacetamide), sulfur compounds (e.g. dimethyl sulfoxide, sulfolane) and mixtures thereof.

The dehydrohalogenating agent includes for example organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide) and the like.

After completion of the reaction, the usual after-treatment is applied, and if necessary, purification by chromatography, distillation, recrystallization, etc. may be applied.

2-Bromo-4,5-dichloroimidazole, a starting material for the present compounds, can be produced, for example, by a method described in U.S. Pat. No. 3,409,606 and J. Heterocycl. Chem., 399 (1967).

Production examples for the present compounds will be shown.

PRODUCTION EXAMPLE 1

To a solution of 0.86 g of 2-bromo-4,5-dichloroimidazole in 5 ml of dimethylformamide was added 96 mg of sodium hydride at room temperature, and after standing for 30 minutes, 0.32 g of methoxymethyl chloride was added dropwise. The resulting mixture was stirred at room temperature for 1 hour, and after adding 40 ml of water, extracted with 30 ml of diethyl ether. Extraction with diethyl ether was repeated two more times, and the ether extract was dried over magnesium sulfate and concentrated to obtain an oily product. This product was purified by column chromatography on silica gel to obtain 0.40 g of 1-methoxymethyl-2-bromo-4,5-dichloroimidazole.

$n_D^{26}$ 1.5402

PRODUCTION EXAMPLE 2

A mixture of 1.06 g of 1-chloromethyl-2-bromo-4,5-dichloroimidazole, 0.54 g of sodium ethoxide and 40 ml of ethanol was heated under reflux for 10 hours. The reaction mixture was then concentrated under reduced pressure to obtain an oily product. This product was purified by column chromatography on silica gel to obtain 0.25 g of 1-ethoxymethyl-2-bromo-4,5-dichloroimidazole.

$n_D^{26}$ 1.5296

PRODUCTION EXAMPLE 3

To a mixture of 1.08 g of 2-bromo-4,5-dichloroimidazole, 0.51 g of triethylamine and about 30 ml of toluene was added dropwise 0.79 g of 4-chlorobutoxymethyl chloride at room temperature, and the resulting mixture was stirred at room temperature for 2 hours. The deposited crystal was filtered off and washed with about 10 ml of toluene. The filtrate thus obtained was concentrated under reduced pressure, and the residual oily product was purified by column chromatography on silica gel to obtain 0.60 g of 1-(4-chlorobutoxymethyl)-2-bromo-4,5-dichloroimidazole.

$n_D^{28}$ 1.5302

Some of the present compounds which can be produced by these methods will be shown in Table 1.

TABLE 1

Bromodichloroimidazole derivatives represented by the formula,

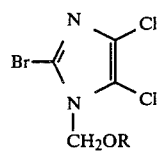

| Compound No. | R | Physical constant |
|---|---|---|
| (1) | —CH₃ | $n_D^{26}$ 1.5402 |
| (2) | —CH₂CH₃ | $n_D^{26}$ 1.5296 |
| (3) | —(CH₂)₂CH₃ | $n_D^{25}$ 1.5216 |
| (4) | —CH(CH₃)₂ | $n_D^{26}$ 1.5194 |
| (5) | —(CH₂)₃CH₃ | $n_D^{25}$ 1.5195 |
| (6) | —CH₂CHCH₃ (with CH₃) | $n_D^{29}$ 1.5124 |
| (7) | —CH₂CH=CH₂ | $n_D^{28}$ 1.5398 |
| (8) | —CHCH₂CH₃ (with CH₃) | $n_D^{25}$ 1.5178 |
| (9) | —CH₂C≡CH | $n_D^{25}$ 1.5545 |
| (10) | —C(CH₃)₃ | $n_D^{26}$ 1.5283 |
| (11) | ~~~Cl (butyl chain) | $n_D^{28}$ 1.5302 |
| (12) | ~~~Br (butyl chain) | $n_D^{22}$ 1.5491 |
| (13) | ~~F (propyl chain) | $n_D^{29}$ 1.5255 |
| (14) | CH(CH₂F)₂ 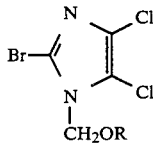 | $n_D^{29}$ 1.5001 |
| (15) | ~~~Cl (propyl chain) | $n_D^{25}$ 1.5472 |
| (16) | ~~~~Cl (pentyl chain) | m.p. 59° C. |
| (17) | isobutyl-Cl | $n_D^{25}$ 1.5396 |
| (18) | isopentyl-Cl | $n_D^{18}$ 1.5276 |
| (19) | —CH₂CH=CHCl | $n_D^{19}$ 1.5565 |
| (20) | —CH₂C(Cl)=CH₂ (with ethyl) | $n_D^{22}$ 1.5530 |
| (21) | ~~~Br (propyl) | $n_D^{24}$ 1.5667 |
| (22) | ~~~~Br (pentyl) | m.p. 78–79° C. |
| (23) | ~~~~~Br (hexyl) | $n_D^{21}$ 1.5495 |
| (24) | ~~~~F (pentyl) | $n_D^{22}$ 1.5231 |
| (25) | ~~~~F (hexyl) | $n_D^{25}$ 1.5190 |
| (26) | CH(CH₃)CH₂Br branched | $n_D^{23}$ 1.5487 |
| (27) | ~~~~I | $n_D^{22}$ 1.5572 |

TABLE 1-continued

Bromodichloroimidazole derivatives represented by the formula,

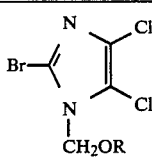

| Compound No. | R | Physical constant |
|---|---|---|
| (28) | ![](/=-Br) | $n_D^{24}$ 1.5785 |

When the present compounds are used as an active ingredient for an insecticidal and/or acaricidal composition, they may be used as such without adding any other ingredients. Generally, however, they are formulated into emulsifiable concentrates, wettable powders, dusts, granules, oil sprays, aerosols, heating fumigants (e.g. mosquito coils, electric mosquito mats, porous ceramic plates), foggings, non-heating fumigants, poisonous baits, etc. by mixing with solid carriers, liquid carriers, gaseous carriers, surface active agents, other auxiliaries for formulation, baits, etc., or impregnating into bases such as mosquito coil carriers, mats, etc.

As described above, the insecticidal composition of the present invention is particularly suitable for the control of cockroaches so that, in using it for such purpose, its insecticidal effect can be developed more efficiently by using it in the form of a fumigant. The fumigant means one of the pesticide formulations which controls pests or fungi by dispersing the active ingredients into atmosphere in some way.

As the form of such fumigant, there may be given, for example, types suitable for non-heating (e.g. mothprofer strip, insecticidal strip, mothball), burning (e.g. "jet" type formulations, "rod" type formulations, mosquito coil), exothermic reaction (e.g. types generating heat by water addition or air oxidation), electric heating (e.g. mat) and the like.

As the mothprofer strip or insecticidal strip, there may be given, for example, strips produced by impregnating the paper, pulp, synthetic resin, etc. with an active ingredient.

As the mothball, there may be given, for example, balls produced by hardening an active ingredient as such.

As a main base for the "jet" type formulations, there are given, for example, mixtures of a nitrate or nitrite and a thermal decomposition-stimulating agent (e.g. salts of an alkaline earth metal or alkali metal), mixtures of a guanidine salt and a thermal decomposition-stimulating agent (e.g. bichromates, chromates), and the like.

As a main base for the "rod" type formulations, there are given, for example, mixtures of a burning agent (e.g. ethyl cellulose, nitrocellulose), a flame-extinguishing agent (e.g. melamine, flour), a filler (e.g. diatomaceous earth) and a vehicle and the like. This mixture is kneaded and then formed into a rod.

As a main base for mosquito coil, there are given, for example, mixture of a burning agent (e.g. wood powder, pyrethrum marc) and a setting agent (e.g. Tabu powder). This mixture is kneaded and then formed into a mosquito coil.

As a main base for the type which generates heat by air oxidation, there are given, for example, mixtures of a heat-generating agent (e.g. sulfides, polysulfides or hydrosulfides of an alkali metal, their hydrated salts), a catalytic substance (e.g. carbon black, activated carbon, charcoal, coke, asphalt) and a filler (e.g. natural fibers, synthetic fibers, synthetic resin foams), and the like.

As a main base for the type which generates heat by water addition, there are given, for example, mixtures of an organic foaming agent (e.g. azodicarbonamide, benzenesulfonyl hydrazide) and a heat-generating agent (e.g. calcium oxide), and the like.

As the mat, there may be given, for example, mats produced by impregnating the porous plate of asbestos, pulp, ceramics, etc. with an active ingredient dissolved in an organic solvent such as acetone.

These compositions contain 0.001 to 95% by weight of the present compound as an active ingredient.

The solid carrier includes for example fine powders or granules of kaolin clay, attapulgite clay, bentonite, terra abla, pyrophyllite, talc, diatomaceous earth, calcite, corn stalk powder, walnut shell powder, urea, ammonium sulfate, synthetic hydrated silicon dioxide and the like. The liquid carrier includes for example aliphatic hydrocarbons (e.g. kerosene), aromatic hydrocarbons (e.g. benzene, toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutyronitrile), acid amides (e.g. dimethylformamide, dimethylacetamide), dimethyl sulfoxide, vegetable oils (e.g. soybean oil, cotton seed oil) and the like. The gaseous carrier includes for example freon gas, LPG (liquefied petroleum gas), dimethyl ether and the like. The surface active agent used for emulsification, dispersion, wetting, etc. includes for example anionic surface active agents such as the salt of alkyl sulfates, alkyl(aryl)sulfonates, dialkyl sulfosuccinates, the salt of polyoxyethylene alkylaryl ether phosphoric acid ester, naphthalenesulfonic acid/formalin condensates, etc., and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation such as fixing agents, dispersing agents, etc. includes for example lignosulfonates, alginates, polyvinyl alcohol, gum arabic, molasses, casein, gelatin, CMC (carboxymethyl cellulose), pine oil, agar, etc. The stabilizer includes for example alkyl phosphates [e.g. PAP (isopropyl acid phosphate), TCP (tricresyl phosphate)], vegetable oils, epoxidized oils, the foregoing surface active agents, antioxidants (e.g. BHT, BHA), fatty acid salts (e.g. sodium oleate, calcium stearate), fatty acid esters (e.g. methyl oleate, methyl stearate) and the like.

Formulation examples will be shown. The present compounds are shown by Compound No. described in Table 1. Parts in the examples are by weight.

FORMULATION EXAMPLE 1

0.2 Part of each of the present compounds (1) and (11), 2 parts of xylene and 97.8 parts of kerosene are mixed to obtain the oil spray of each compound.

FORMULATION EXAMPLE 2

Ten parts of each of the present compounds (1) to (28), 14 parts of polyoxyethylene styrylphenyl ether, 6 parts of calcium dodecylbenzenesulfonate and 70 parts of xylene are well mixed to obtain the emulsifiable concentrate of each compound.

FORMULATION EXAMPLE 3

Twenty parts of each of the present compounds (3) and (12), 10 parts of fenitrothion, 3 parts of calcium lignosulfonate, 2 parts of sodium lauryl sulfate and 65 parts of synthetic hydrated silicon dioxide are well pulverized and mixed together to obtain the wettable powder of each compound.

FORMULATION EXAMPLE 4

One part of each of the present compounds (4) and (13), 2 parts of Carbaryl, 87 parts of kaolin clay and 10 parts of talc are well pulverized and mixed together to obtain the dust of each compound.

FORMULATION EXAMLE 5

Five parts of each of the present compounds (5) and (15), 1 part of synthetic hydrated silicon dioxide, 2 parts of calcium lignosulfonate, 30 parts of bentonite and 62 parts of kaolin clay are well pulverized and mixed together, well kneaded with water, granulated and then dried to obtain the granule of each compound.

FORMULATION EXAMPLE 6

0.05 Parts of each of the present compounds (6) and (16), 0.2 part of tetramethrin, 0.05 part of resmethrin, 7 parts of xylene and 32.7 parts of deodorized kerosene are well mixed into a solution. The solution is filled in an aerosol container, and after attaching a valve portion to the container, 60 parts of a propellant (liquefied petroleum gas) is charged therein through the valve under pressure to obtain the aerosol of each compound.

FORMULATION EXAMPLE 7

0.3 Gram of each of the present compounds (7) and (17) and 0.3 g of the d-trans-chrysanthemate of allethrin are dissolved in 20 ml of methanol. This solution and 99.4 g of a mosquito coil carrier, which is a 3:5:1 mixture of Tabu powder, Pyrethrum marc and wood powder, are uniformly mixed with stirring. After evaporating methanol, 150 ml of water is added to the residue, and the mixture is well kneaded, shaped and dried to obtain the mosquito coil of each compound.

FORMULATION EXAMPLE 8

One hundred mg of each of the present compounds (1) to (28) is dissolved in a proper amount of acetone, and a porous ceramic plate of 4.0 cm×4.0 cm×1.2 cm (thick) is impregnated with this solution to obtain the heating fumigant of each compound.

These compositions are used as such or as aqueous dilute solutions. Also, they may be used in mixture with other insecticides, acaricides, namatocides, fungicides, herbicides, plant growth regulators, fertilizers, soil improvers and the like.

When the present compounds are used in the form of emulsifiable concentrate or wettable powder as an insecticidal and/or acaricidal composition, their application concentration is 10 to 10000 ppm. When they are used in the form of dust, granule, oil spray or aerosol, they are applied as such without dilution.

Test examples will be shown. Compounds used as a control are shown by Compound symbol in Table 2.

TABLE 2

| Compound symbol | Structural formula | Name |
|---|---|---|
| (A) | (pyrazine with Cl, Cl, Cl substituents and N-CH$_2$OC$_5$H$_{11}$(n)) | Compound described in B. P. No. 1,316,665 and U.S. Pat. No. 3,674,874. |
| (B) | (pyrazine with Cl, Cl, Cl substituents and N-CH$_2$OCH(CH$_3$)$_2$) | Compound described in U.S Pat. No. 3,674,874. |
| (C) | (phenyl-OCNHCH$_3$ with OCH(CH$_3$)$_2$) | Propoxur |
| (D) | CH$_3$O\P(=S)-SCHCOOC$_2$H$_5$ / CH$_3$O    CH$_2$COOC$_2$H$_5$ | Malathion |

TEST EXAMPLE 1

On the bottom of a polyethylene cup of 5.5 cm in diameter was placed a piece of filter paper of the same size as the bottom. 0.7 Milliliter of the 200-fold aqueous dilute solution (corresponding to 500 ppm of active ingredient) of emulsifiable concentrates, prepared from the present compounds according to Formulation example 2, was dropped down to the filter paper, and 30 mg of sucrose was uniformly placed on the filter paper as bait. Thereafter, 10 female adult houseflies (*Musca domestica*) were liberated in the cup which was then covered with a lid. After 24 hours, the number of the dead and alive was examined to obtain a mortality (two replications).

The result is shown in Table 3.

TABLE 3

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (13) | 100 |
| (15) | 100 |
| (17) | 100 |
| (19) | 100 |
| (20) | 100 |
| (21) | 100 |
| (24) | 100 |
| (25) | 100 |

TEST EXAMPLE 2

The rice seedlings (about 12 cm in length) were dipped for 1 minute in the 200-fold aqueous dilute solution (corresponding to 500 ppm of active ingredient) of emulsifiable concentrates, prepared from the present compounds and the control according to Formulation example 2. After air-drying, the seedlings were placed in a test tube, and 10 adult green rice leafhoppers, Nephotettix cincticeps, (resistant strain) were liberated therein. After one day, the number of the dead and alive was examined to obtain a mortality (two replications).

The result is shown in Table 4.

TABLE 3-continued

| Test compound | Mortality (%) |
| --- | --- |
| No treatment | 0 |

TABLE 4

| Test compound | Mortality (%) |
| --- | --- |
| (3) | 100 |
| (5) | 100 |
| (6) | 100 |
| (A) | 60 |
| (B) | 20 |
| (D) | 50 |
| No treatment | 5 |

TEST EXAMPLE 3

On the bottom of a polyethylene cup of 5.5 cm in diameter was placed a piece of filter paper of the same size as the bottom. 0.7 Milliliter of an aqueous dilute solution of prescribed concentrations, prepared from the emulsifiable concentrates of the present compounds and the control formulated according to Formulation example 2, was dropped down to the filter paper, and 30 mg of sucrose was placed on the filter paper as bait. Thereafter, 10 male adults of German cockroaches (Blattella germanica) were liberated in the cup which was then covered with a lid. After 72 hours, the number of the dead and alive was examined to obtain $LC_{50}$ value (50% lethal concentration) (two replications).

The result is shown in Table 5.

TABLE 5

| Test compound | $LC_{50}$ (ppm) |
| --- | --- |
| (1) | 2.7 |
| (2) | 3.3 |
| (3) | 7.4 |
| (4) | 2.7 |
| (5) | 6.1 |
| (7) | 8.7 |
| (9) | 8.7 |
| (11) | 21 |
| (12) | 23 |
| (13) | 14 |
| (15) | 17 |
| (16) | 17 |
| (17) | 21 |
| (18) | 23 |
| (19) | 8.7 |
| (20) | 21 |
| (21) | 19 |
| (22) | 22 |
| (24) | 11 |
| (25) | 8.7 |
| (28) | 9.0 |
| (A) | 30 |
| (C) | ≈150 |

TEST EXAMPLE 4

The present compounds and the control were each diluted with acetone to prescribed concentrations and topically applied to the ventral thorax of the male adults of German cockroaches (Blattella germanica) at a rate of 1 μl/adult. After application, the adults were bred on bait and water in a polyethylene cup. After two days, the number of the dead and alive was examined to obtain $LD_{50}$ value (50% lethal dosage) (10 adults per group; two replications).

The result is shown in Table 6.

TABLE 6

| Test compound | $LD_{50}$ (μg/ ♂) |
| --- | --- |
| (1) | 0.18 |
| (2) | 0.25 |
| (3) | 0.33 |
| (4) | 0.17 |
| (5) | 0.25 |
| (7) | 0.21 |
| (9) | 0.16 |
| (12) | 0.37 |
| (13) | 0.22 |
| (19) | 0.27 |
| (21) | 0.18 |
| (25) | 0.32 |
| (A) | >1 |

TEST EXAMPLE 5

Four polyethylene cups (inside diameter, 10 cm; height, 8 cm) coated with butter at the inside surface were set at the four corners, respectively, of the bottom of a (70 cm)³ glass chamber (0.34 m³). Ten male adults per group of German cockroaches (Blattella germanica) were liberated in each of two polyethylene cups, and 10 female adults per group of the insects were liberated in each of the remaining two. An electric heater was set at the center of the bottom of the glass chamber, and each of the porous ceramic plates impregnating the present compounds and the control according to Formulation example 8 (13.7 mg/mat; 40 mg/m³), was placed thereon. The mat was heated to about 200° C. by applying current for 20 minutes. Eighty minutes after current application was started, the cups containing the test insects were taken out of the chamber, and the test insects were bred on water and bait. After two days, the number of the dead and alive was examined to obtain a mortality.

The result is shown in Table 7.

TABLE 7

| Test compound | Mortality (%) |
| --- | --- |
| (1) | 100 |
| (2) | 100 |
| (3) | 100 |
| (4) | 100 |
| (6) | 100 |
| (7) | 100 |
| (8) | 100 |
| (9) | 100 |
| (10) | 100 |
| (11) | 100 |
| (12) | 100 |
| (13) | 100 |
| (15) | 100 |
| (16) | 100 |
| (17) | 100 |
| (18) | 100 |
| (21) | 100 |
| (22) | 100 |
| (23) | 97.5 |
| (25) | 100 |

TABLE 7-continued

| Test compound | Mortality (%) |
| --- | --- |
| (26) | 100 |
| (27) | 100 |
| (28) | 97.5 |
| (A) | 47.5 |
| (C) | 0 |

TEST EXAMPLE 6

At the bottom of a (183 cm)$^3$ Peet Grady's chamber (6.1 m$^3$) were placed three polyethylene cups (inside diameter, 10 cm; height, 8 cm) coated with butter at the inside surface, and 20 adult German cockroaches (10 males and 10 females) (*Blattella germanica*) were liberated in each cup. An electric heater was set at the center of the bottom of the chamber, and each of the porous ceramic plates impregnating the present compounds and the control according to Formulation example 8 (61 mg/mat; 10 mg/m$^3$), was placed thereon. The plate was heated to about 200° C. by applying current for 70 minutes. The number of knocked-down insects with the lapse of time was examined to obtain KT$_{50}$ value (50% knocked-down time). Eighty minutes after current application was started, the cups containing the test insects were taken out of the chamber, and the test insects were bred on water and bait. After three days, the number of the dead and alive was examined to obtain a mortality.

The result is shown in Table 8.

TABLE 8

| Test compound | KT$_{50}$ (minute) | Mortality (%) |
| --- | --- | --- |
| (12) | 57' | 87.5 |
| (21) | 72' | 95 |
| (A) | >80' | 0 |
| (C) | >80' | 0 |

TEST EXAMPLE 7

The female adults of carmine spider mites (*Tetranychus cinnabarinus*) were made parasitic on the leaves of potted kidney bean (at the primordial leaf stage) which had elapsed 7 days after sowing at a rate of 10 adults/leaf, and placed in a constant-temperature room kept at 25° C. After 6 days, the emulsifiable concentrate of the present compounds formulated according to Formulation example 2 was diluted with water so that the concentration of active ingredient was 500 ppm, and 10 ml of the aqueous dilute solution was sprayed onto the plant on a turn table by a spray gun. At the same time, the soil in the pot was drenched with 2 ml of the same solution. After 8 days, the degree of damage of the plant by the mites was examined.

The degree of damage is expressed in the following three grades:

—: Any damage is not observed.
+: Slight damage is observed.
++: The same damage as in the untreated plot is observed.

The result is shown in Table 9.

TABLE 9

| Test compound | Degree of damage |
| --- | --- |
| (2) | −~+ |
| (7) | −~+ |
| (9) | − |

TABLE 9-continued

| Test compound | Degree of damage |
| --- | --- |
| (13) | − |
| (14) | − |
| (24) | −~+ |
| No treatment | ++ |

What is claimed is:

1. A bromodichloroimidazole derivative represented by the formula,

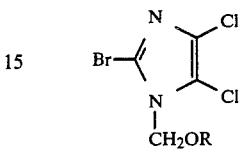

wherein R represents a C$_1$–C$_3$ alkyl, C$_2$–C$_5$ alkyl substituted by one or more halogen atoms, C$_3$ alkenyl, or C$_3$ alkynyl.

2. The bromodichloroimidazole derivative according to claim 1, wherein R is a C$_1$ or C$_3$ alkyl, C$_3$ alkenyl or C$_3$ alkynyl group.

3. The bromodichloroimidzole derivative according to claim 1, wherein R is a C$_2$–C$_4$ alkyl group substituted by one or more halogen atoms.

4. 1-Methoxymethyl-2-bromo-4,5-dichloroimidazole.

5. 1-n-Propyloxymethyl-2-bromo-4,5-dichloroimidazole.

6. 1-Isopropyloxymethyl-2-bromo-4,5-dichloroimidazole.

7. 1-(4-Bromobutyloxymethyl)-2-bromo-4,5-dichloroimidazole.

8. An insecticidal and/or acaricidal composition which comprises as an active ingredient an insecticidally and/or acaricidally effective amount of a bromodichloroimidazole derivative represented by the formula,

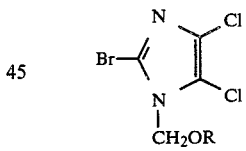

wherein R represents a C$_1$–C$_3$ alkyl, C$_2$–C$_5$ alkyl substituted by one or more halogen atoms, C$_3$ alkenyl, or C$_3$ alkynyl, and an inert carrier.

9. The insecticidal composition according to claim 8, wherein the composition is a form of a fumigant for cockroaches.

10. The insecticidal composition according to claim 9, wherein the bromodichloroimidazole derivative is 1-n-propyloxymethyl-2-bromo-4,5-dichloroimidazole.

11. The insecticidal composition according to claim 9, wherein the bromodichloroimidazole derivative is 1-(C$_2$–C$_4$ haloalkyloxymethyl)-2-bromo-4,5-dichloroimidazole.

12. The insecticidal composition according to claim 9, wherein the bromodichloroimidazole derivative is 1-(4-bromobutyloxymethyl)-2-bromo-4,5-dichloroimidazole.

13. A method for killing insects and/or acarids which comprises applying an insecticidally and/or acaricidally effective amount of a bromodichloroimidazole derivative represented by the formula

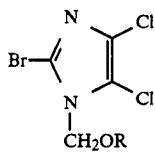

wherein R represents a $C_1$–$C_3$ alkyl, $C_2$–$C_5$ alkyl substituted by one or more halogen atoms, $C_3$ alkenyl, or $C_3$ alkynyl, to the insects and/or acarids.

14. The method for killing insects according to claim 13, wherein the insects are cockroches.

15. The method for killing insects according to claim 14, wherein R is a $C_1$ or $C_3$ alkyl, $C_3$ alkenyl or $C_3$ alkynyl group.

16. The method for killing insects according to claim 14, wherein the bromodichloroimidazole derivative is 1-($C_2$–$C_4$ haloalkyloxymethyl)-2-bromo-4,5-dichloroimidazole.

17. The method for killing insects according to claim 14, wherein the bromodichloroimidazole derivative is 1-methoxymethyl-2-bromo-4,5-dichloroimidazole.

18. The method for killing insects according to claim 14, wherein the bromodichloroimidazole derivative is 1-n-propyloxymethyl-2-bromo-4,5-dichloroimidazole.

19. The method for killing insects according to claim 14, wherein the bromodichloloimidazole derivative is 1-isopropyloxymethyl-2-bromo-4,5-dichloroimidazole.

20. The method for killing insects according to claim 14, wherein the bromodichloroimidazole derivative is 1-(4-bromobutyloxymethyl)-2-bromo-4,5-dichloroimidazole.

* * * * *